United States Patent
Hong et al.

(10) Patent No.: US 11,938,220 B2
(45) Date of Patent: Mar. 26, 2024

(54) SUSTAINED-RELEASE ANESTHETIC COMPOSITIONS AND METHODS OF PREPARATION THEREOF

(71) Applicants: TLC Biopharmaceuticals, Inc., South San Franciso, CA (US); Taiwan Liposome Co., Ltd., Taipei (TW)

(72) Inventors: Keelung Hong, South San Francisco, CA (US); Yun-Long Tseng, Taipei (TW); Chun-Yen Lai, Taipei (TW); Wan-Ni Yu, Taipei (TW); Hao-Wen Kao, Taipei (TW); Yi-Yu Lin, Taipei (TW)

(73) Assignees: Taiwan Liposome Co., Ltd, Taipei (TW); TLC Biopharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 17/043,920

(22) PCT Filed: Mar. 30, 2019

(86) PCT No.: PCT/US2019/025064
§ 371 (c)(1),
(2) Date: Sep. 30, 2020

(87) PCT Pub. No.: WO2019/191731
PCT Pub. Date: Oct. 3, 2019

(65) Prior Publication Data
US 2021/0128475 A1 May 6, 2021

Related U.S. Application Data

(60) Provisional application No. 62/650,912, filed on Mar. 30, 2018.

(51) Int. Cl.
| | | |
|---|---|---|
| *A61K 9/127* | (2006.01) | |
| *A61K 9/00* | (2006.01) | |
| *A61K 31/445* | (2006.01) | |
| *A61K 47/24* | (2006.01) | |
| *A61K 47/28* | (2006.01) | |
| *A61P 23/02* | (2006.01) | |

(52) U.S. Cl.
CPC .......... *A61K 9/1277* (2013.01); *A61K 9/0014* (2013.01); *A61K 31/445* (2013.01); *A61K 47/24* (2013.01); *A61K 47/28* (2013.01); *A61P 23/02* (2018.01)

(58) Field of Classification Search
None
See application file for complete search history.

(56) References Cited

U.S. PATENT DOCUMENTS

| | | | |
|---|---|---|---|
| 6,926,905 | B2 | 8/2005 | Grant et al. |
| 9,877,919 | B2 * | 1/2018 | DeRosa ................ A61K 38/44 |
| 2002/0114835 | A1 | 8/2002 | Sackler et al. |
| 2004/0052836 | A1 | 3/2004 | Li et al. |
| 2015/0250724 | A1 * | 9/2015 | Yamashita ........... A61K 9/0019 604/272 |
| 2015/0359891 | A1 * | 12/2015 | Chen .................... A61K 31/445 514/447 |
| 2020/0188374 | A1 | 6/2020 | Hong et al. |

FOREIGN PATENT DOCUMENTS

| | | |
|---|---|---|
| CN | 111182889 A | 5/2020 |
| WO | 2013146386 A1 | 10/2013 |

OTHER PUBLICATIONS

Bakonyi et al., "DSC for evaluating the encapsulation efficiency of lidocaine-loaded liposomes compared to the ultracentrifugation method," J Therm Anal Calorim, 2017, 130:1619-1625.
Li et al., "A Novel Method for the Preparation of Liposomes: Freeze Drying of Monophase Solutions," J Pharm Sci. 2004, 93(6):1403-1414.
Migally, "Effect of castor oil and benzyl benzoate used as a vehicle for antiandrogens on the adrenal cortex," Arch Androl, 1979, 2(4):365-369.
Van Osdol et al., "Effects of the anesthetic dibucaine on the kinetics of the gel-liquid crystalline transition of dipalmitoylphosphatidylcholine multilamellar vesicles," Biophys J, 1992,63(4):1011-1017.
Van Osdol et al., "Relaxation dynamics of the gel to liquid-crystalline transition of phosphatidylcholine bilayers, Effects of chainlength and vesicle size," Biophys J, 199,59(4):775-785.
Office Action in Russian Application No. 2020133638 (dated Nov. 28, 2023) and English translation, 10 pages.

* cited by examiner

*Primary Examiner* — Celeste A Roney
(74) *Attorney, Agent, or Firm* — Finnegan, Henderson, Farabow, Garrett & Dunner, LLP

(57) ABSTRACT

Provided is an anesthetic composition for locally administering a local anesthetic agent to a subject in need thereof. The anesthetic composition has a lipid based complex prepared by hydrating a lipid cake containing a local anesthetic agent and a lipid mixture with an aqueous buffer solution at a pH higher than 5.5. Also provided is a method to prepare an anesthetic composition using a simpler and more robust for large-scale manufacture and for providing a high molar ratio of local anesthetic agent to phospholipid content as compared to the prior art. This anesthetic composition has a prolonged duration of efficacy adapted to drug delivery.

17 Claims, 4 Drawing Sheets

SUSTAINED-RELEASE ANESTHETIC COMPOSITIONS AND METHODS OF PREPARATION THEREOF

RELATED APPLICATIONS

This application is a national stage application under 35 U.S.C. § 371 of International Application No. PCT/US2019/025064, filed Mar. 30, 2019, which designated the U.S. and claims the benefit of priority of U.S. Provisional Application No. 62/650,912, filed Mar. 30, 2018, each of which is hereby incorporated by reference in its entirety.

BACKGROUND

Technical Field

The present disclosure relates to a drug delivery system for delivery of a sustained-release anesthetic composition. The present disclosure relates to a method of preparing the drug delivery system. The present disclosure also relates to a sustained-release pharmaceutical composition adapted to a drug delivery system, which has a prolonged duration of efficacy.

Description of Related Art

Several technologies for developing sustained-released local anesthetics have been reported. For examples, dibucaine free base, dibucaine HCl, and bupivacaine HCl were incorporated into polymer matrices with copolymer 1,3-bis(p-carboxyphenoxy)propane-sebacic acid anhydride (1:4) to achieve sustained release of the drug. On the other hand, multivesicular liposomal (MVL) local anesthetics prepared by a complex procedure (U.S. Pat. No. 8,182,835) are used for delivery of local anesthetics.

To achieve improved efficacy of drug via lipid based delivery vehicle with high entrapment of drug, i.e., a high drug-to-lipid ratio, conventional manufacture of the lipid-based formulations with desired high entrapment of the drug generally involves tedious procedures and high production costs. There is therefore an unmet need for sustained-release local anesthetics with improved efficacy and obtained by simplified manufacturing processes.

SUMMARY

The present disclosure provides a sustained-release anesthetic composition or a method of preparing the same by using one-step lyophilization to obtain a lipid cake comprising a local anesthetic agent and a lipid mixture, and then hydrating the lipid cake with a pH controlled buffer solution to form a lipid based complex containing the local anesthetic agent and the lipid mixture. This sustained-release anesthetic composition provides a rapid onset of anesthesia and a prolonged duration of local anesthesia with minimal toxicity. In some embodiments, the local anesthetic agent is an amide-type anesthetic.

In some embodiments, the local anesthetic agent is ropivacaine. Other local anesthetic agents that may be used include lidocaine, bupivacaine, and levobupivacaine.

In some embodiments, the present disclosure provides a simple and robust manufacturing process for preparing an anesthetic composition for locally administering local anesthetics into a subject in need, wherein a hydration step in the process can be performed in an ambient environment.

In some embodiments, the lipid cake is formed with a phospholipid to allow being rehydrated with a buffer to obtain a desired sustained-release anesthetic composition with high association efficiency of the local anesthetic agent at an ambient temperature without elevating the temperature, which causes extra expense on energy or inconvenience in clinical use.

According to the present disclosure, the lipid cake comprises a local anesthetic agent and a lipid mixture including at least one neutral saturated phospholipid comprising saturated fatty acids with long carbon chain with a carbon number no greater than 18, whereby the lipid cake can be preserved easily and the anesthetic composition can be prepared by mixing the lipid cake with a buffer in a manufacture plant or prior to clinical use under a predetermined controlled condition, e.g., at an ambient temperature. In some embodiments, the saturated fatty acids with long carbon chains have a carbon number of 14, 16, or 18.

In some embodiments, the lipid cake according to the present disclosure is prepared by dissolving apolar ropivacaine, phospholipid, and cholesterol in a solvent system, e.g., tert-butanol alone or a tert-butanol/water cosolvent, followed by removing the solvent system using a lyophilization technique.

The pH value of a pharmaceutically acceptable buffer solution can nevertheless be selected to adjust the ratio of entrapped local anesthetic agent to untrapped local anesthetic agent in the anesthetic composition. In certain embodiments, the molar ratio of local anesthetic agent to phospholipid ($mol_{drug}$:$mol_{phospholipid}$) in the lipid based complex of the anesthetic composition is at least 0.5:1, and can provide a sufficient amount of the local anesthetic agent to a subject in need thereof to prolong the duration of anesthesia after in vivo local administration. In addition, limiting the amount of untrapped local anesthetic agent can achieve rapid onset anesthesia with minimized maximum plasma concentration ($C_{max}$) exposure.

In some embodiments, the present disclosure also provides methods for producing analgesia or pain relief in a subject in need thereof, comprising: administering to the subject the anesthetic composition according to the present disclosure.

In some embodiments, the present disclosure provides methods for managing pain or for prophylactic treatment of pain in a subject, comprising: administering to the subject the anesthetic composition according to the present disclosure.

Other objectives, advantages, and novel features of the disclosure will become more apparent from the following detailed description when taken in conjunction with the accompanying drawings.

DETAILED DESCRIPTION

Figure 1A:
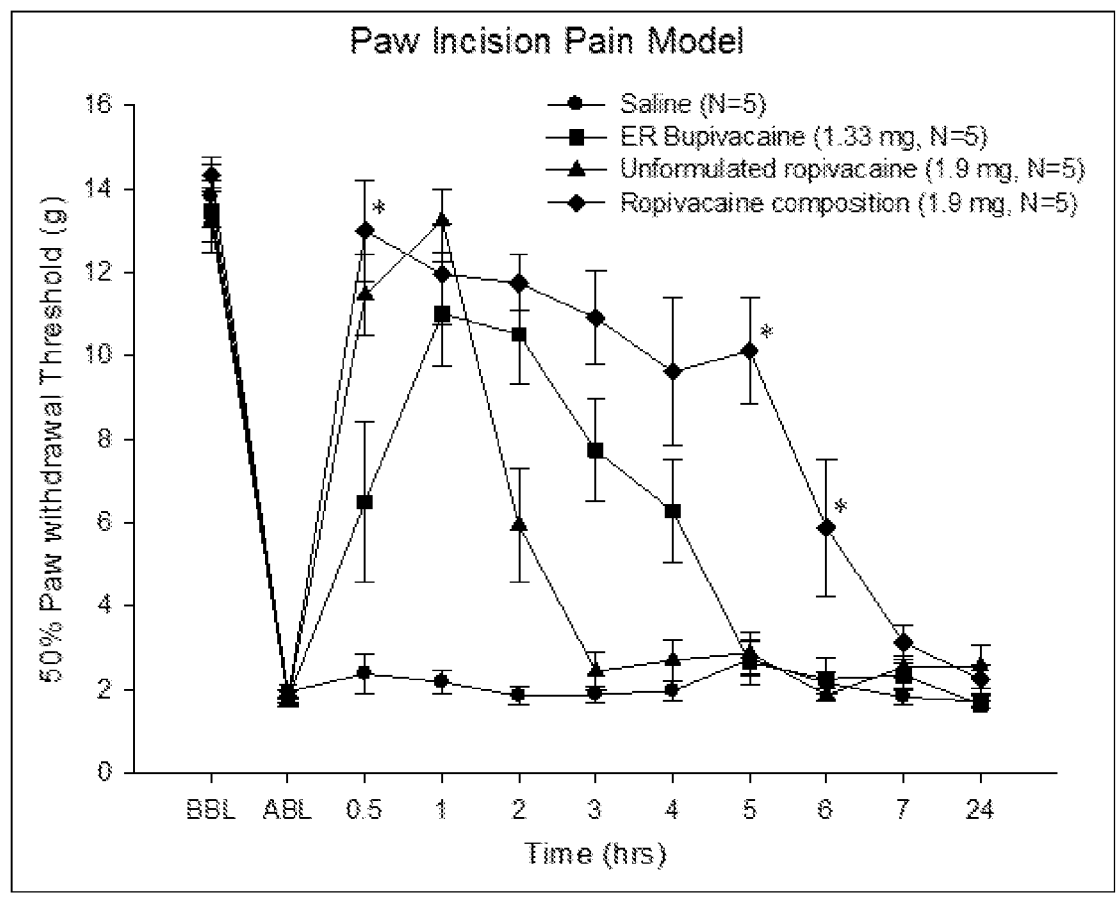
FIG. 1A is a graph depicting 50% paw withdrawal threshold by a Von Frey test; wherein an anesthetic composition in accordance with the present disclosure (Ropivacaine composition) is our test article and ropivacaine injectable solution (unformulated ropivacaine) and commercial extended release liposomal bupivacaine (ER Bupivacaine) are used as reference articles. Saline, Ropivacaine composition, Ropivacaine injectable solution, and ER Bupivacaine were intraplantarly administered after paw incision; the error bars represent the standard error of mean (SEM); and *:P<0.05 when compared to ER Bupivacaine group; BBL=Before surgery baseline; ABL=After surgery baseline.

As employed above and throughout the disclosure, the following terms, unless otherwise indicated, shall be understood to have the following meanings.

As used herein, the singular forms "a", "an," and "the" include the plural reference unless the context clearly indicates otherwise.

All numbers herein may be understood as modified by "about," which, when referring to a measurable value such as an amount, a temporal duration, and the like, is meant to encompass variations of ±10%, ±5%, ±1%, or ±0.1% from the specified value, as such variations are appropriate to obtain a desired amount of drug, unless otherwise specified.

"Association efficiency" (AE) represents the amount of drug substance entrapped in formed lipid based complex containing local anesthetic agents in an anesthetic composition and is calculated by the ratio of the amount of a drug substance in a separated lipid based complex to the amount of that drug substance in the anesthetic composition. Separated lipid based complex can be obtained from the anesthetic composition by any method known in the art. In some embodiments, separated lipid based complex are obtained from a prepared anesthetic composition by centrifugation methods, e.g., traditional centrifugation, density gradient centrifugation, differential centrifugation, or by filtration methods, e.g., diafiltration, gel filtration, membrane filtration.

The term "treat", "treating," or "treatment" as used herein, includes preventative (e.g. prophylactic), palliative, and curative methods, uses, or results. The terms "treatment" or "treatments" can also refer to compositions or medicaments. The term "treating" encompasses reducing or delaying one or more symptoms or signs of pain or the complete amelioration of pain as detected by known techniques. Art recognized methods are available to evaluate pain and symptoms of pain, such as pain score and 50% paw withdrawal threshold. For example, a disclosed method of use the sustained-release anesthetic composition is considered as a target treatment if there is at least 1% reduction in one or more symptoms of pain in a subject when compared to the subject prior to treatment or control subjects. Thus, the reduction can be about a 5, 10, 20, 30, 40, 50, 60, 70, 80, 90, or 100% reduction, or any amount of reduction in between these values.

Local Anesthetic Agents

"Local anesthetic agents" as used herein include one or more groups of substances causing loss of sensation in a circumscribed area of a subject caused by depression of excitation in nerve endings or inhibition of the conduction process in peripheral nerves. In some embodiments, the local anesthetic agents are amide-type anesthetics. The typical amide-type anesthetic structure contains a lipophilic part and a hydrophilic part that connect by an —NHCO— linkage. Suitable amide-type anesthetics include, but are not limited to, lidocaine, bupivacaine, levobupivacaine, ropivacaine, mepivacaine, pyrrocaine, articaine, and prilocaine. In certain embodiments, the local anesthetic agent is ropivacaine base.

Lipid Cake

The lipid cake comprises a lipid mixture and one or more local anesthetic agents, which can be manufactured, stored long-term so as to extend the shelf life of the composition, and hydrated immediately prior to clinical use in an ambient environment. The lipid mixture described above can comprise one or more phospholipids without sterol or can comprise one or more phospholipids with a mole percentage of sterol, particularly to cholesterol, of no more than 50% relative to the amount of the total lipid mixture. In certain embodiments, the mole percentage of cholesterol on the basis of the lipid mixture is from about 0% to 50%, and optionally from about 25% to 40%, or 33% to 35%. In some embodiments, the phospholipid(s) and cholesterol are at a molar ratio of from 1:1 to 3:1.

The lipid cake can be prepared by 1) dissolving a lipid mixture and one or more local anesthetic agents in a solvent system to form a homogeneous solution comprising one or more solvents, and 2) removing the solvent(s) to solidify the formulation of the lipid mixture and the local anesthetic agent(s). Solvent removal can be performed using known techniques such as freeze drying (lyophilization). Examples of solvent systems suitable for freeze drying include, but are not limited to, tert-butanol and tert-butanol/water cosolvent systems with or without other non-aqueous solvents such as acetone, acetonitrile, ethanol, n-propanol, isopropanol, n-butanol, methanol, dichloromethane, dimethyl sulfoxide, and carbon tetrachloride.

Anesthetic Composition

The term "anesthetic composition" refers to a product suitable for local administration. In certain embodiments, an anesthetic composition comprises a lipid based complex and untrapped local anesthetic agent. In some embodiments, the lipid based complex includes multilamellar vesicles and a local anesthetic agent entrapped in the multilamellar vesicles. The term "entrap" or "entrapment" refers to the bilayer membrane of multilamellar vesicles encapsulating, embedding, or associating with a target drug substance.

The particle size distribution of the lipid based complex according to the present disclosure can be determined by various known methods in the art. In some embodiments, the average particle size of the lipid based complex of the anesthetic composition is no less than 1 μm; and optionally, is more than 5 μm, such as at a range from 5 μm to 50 μm, or from 10 μm to 25 μm. Alternatively, the volume median particle diameter (D50) of the lipid based complex of the anesthetic composition is no less than 1 μm; and, optionally, is not less than 5 μm, such as at a range from 5 μm to 50 μm, 5 μm to 40 μm, 5 μm to 30 μm, 5 μm to 20 μm, or 5 to 15 μm. In some embodiments, the median particle diameter (D50) refers to a particle diameter at which the cumulative percentage of lipid based complex made of the agglomerated particles being 50% in the cumulative particle size distribution is 5 µm or more or 7 µm or more. In some embodiments, the median particle diameter (D50) refers to a particle diameter at which the cumulative percentage of lipid based complex made of the agglomerated particles being 50% in the cumulative particle size distribution is 25 µm or less, 20 µm or less, or 15 µm or less.

In some embodiments, a particle diameter at a cumulative percentage of 90% in a cumulative particle size distribution (D90) of the lipid based complex of the anesthetic composition is not less than 10 µm, such as at a range from 10 µm to 300 µm, from 20 µm to 200 µm, or from 20 µm to 100 µm. In addition, the lower limit value of D90 is not particularly limited to 25 µm or more or 30 µm or more. In addition, the shape of the agglomerated particle of the lipid based complex=for improving association efficiency per unit dosage is not particularly limited.

To prepare the anesthetic composition for use, the lipid cake is hydrated with an aqueous buffer solution at a pH value no less than 5.5, 5.6, 5.7, 5.8, 5.9, 6.0, 6.1, 6.2, 6.3, 6.4, 6.5, 6.6, 6.7, 6.8, 6.9, or 7.0. In some embodiments, the aqueous buffer solution is at a pH range of from 5.5 to 8.0, and optionally of from 6.0 to 7.8, 6.0 to 7.5, 6.3 to 7.5, 6.5 to 7.5, 6.7 to 7.5, or 6.8 to 7.5.

Suitable aqueous buffer solutions according to the present disclosure include, but are not limited to, citrate, acetate, malate, piperazine, succinate, 2-(N-morpholino)ethanesulfonic acid (MES), histidine, bis-tris, phosphate, ethanolamine, N-(2-acetamido)iminodiacetic acid (ADA), carbonate, N-(2-acetamido)-2-aminoethanesulfonic acid (ACES), 1,4-piperazinediethanesulfonic acid (PIPES), 3-morpholino-2-hydroxypropanesulfonic acid (MOPSO), imidazole, N,N-bis(2-hydroxyethyl)-2-aminoethanesulfonic acid (BES), 4-(2-hydroxyethyl)piperazine-1-ethanesulfonic acid (HEPES), triethanolamine, lysine, tris, and glycylglycine. The amount of untrapped amide-type anesthetic in the composition can be adjusted based on the distribution-coefficient of the anesthetic by selecting an appropriate pH value for the aqueous buffer solution based on the clinical indication and the total injection dosage.

In some embodiments, the aqueous buffer solution comprises histidine at a concentration ranging from 1 mM to 200 mM, from 10 mM to 150 mM, or from 40 mM to 120 mM.

In some embodiments, the aqueous buffer solution comprises phosphate at a concentration ranging from 1 mM to 200 mM, from 10 mM to 180 mM, or from 40 mM to 160 mM.

The amount of untrapped amide-type anesthetic is a function of the association efficiency (AE) of the anesthetic composition, which is determined by a centrifugation method. Mathematically, the amount of untrapped amide-type anesthetic is expressed as follows:

$$A_{untrapped} = A_{total} \times (1-AE)$$

wherein $A_{untrapped}$ is the amount of untrapped amide-type anesthetic; $A_{total}$ is the total amount of amide-type anesthetic in the anesthetic composition; and AE is obtained by dividing the amount of amide-type anesthetic entrapped in lipid based complex by the total amount of amide-type anesthetic in the anesthetic composition. AE according to the present disclosure is at least 60%, and, optionally, from 70% to 99%.

In certain embodiments, the molar ratio of amide-type anesthetic to phospholipid ($mol_{drug}:mol_{phospholipid}$, D:PL) of the lipid base complex is at least 0.5:1, including but not limited to 0.6:1, 0.7:1, 0.8:1, 0.9:1, 1.0:1, 1.1:1, 1.2:1, 1.3:1, 1.4:1 or 1.5:1. In certain embodiments, the median diameter (D50) of the lipid based complex is not less than 1 µm, and, optionally, is not less than 5 µm, such as at a range from 5 µm to 50 µm, 5 µm to 40 µm, 5 µm to 30 µm, 5 µm to 20 µm or 5 µm to 15 µm; D90 of the lipid based complex is not less than 10 µm, such as at a range from 10 µm to 300 µm, from 20 µm to 200 µm, or from 20 µm to 100 µm.

The amide-type anesthetic concentration of the anesthetic composition should be higher than 2 mg/mL to achieve a clinical therapeutic benefit. Suitable amide-type anesthetic concentrations include but are not limited to from 2 mg/mL to 30 mg/mL and from 10 mg/mL to 20 mg/mL. The restricted amount of untrapped anesthetic in the anesthetic compositions of the disclosure can provide the benefit of achieving a higher maximum tolerance dosage (depending on the plasma anesthetic concentration that causes central nervous system and cardiovascular system toxicity) and can be used to provide rapid-onset efficacy.

For clinical use, AE in certain embodiments of the disclosure ranges from 70% to 99.9%, 75% to 99.5%, 80% to 99.5%, 85% to 99.5%, 90% to 99.5%, or 95% to 99.5%. The remaining lipid based complex act as a depot to release the amide-type anesthetic into the local environment gradually in a manner that maintains the therapeutically effective dosage at the local site. In some embodiments, the half-life of ropivacaine, derived from a single subcutaneous administration of a ropivacaine composition according to the disclosure, is prolonged at least 10-fold compared to that of unformulated ropivacaine. The duration of the anesthetic effect after administration of the ropivacaine composition of the disclosure significantly extends beyond that of unformulated ropivacaine.

Multilamellar Vesicle

The term "multilamellar vesicle" as used herein refers to a particle characterized by having an aqueous interior space sequestered from an outer medium by a membrane of one or more bilayers forming a vesicle. Bilayer membranes of multilamellar vesicles are typically formed by lipids, i.e., amphiphilic molecules of synthetic or natural origin that comprise spatially separated hydrophobic and hydrophilic domains. In certain embodiments of the present disclosure, a multilamellar vesicle in which more than one lipid bilayer forms the membrane.

In general, bilayer membrane of multilamellar vesicles comprises a lipid mixture comprising dialiphatic chain lipids, such as phospholipids, diglycerides, dialiphatic glycolipids; single lipids, such as sphingomyelin and glycosphingolipid; steroids, such as cholesterol and derivates thereof; and combinations thereof. Examples of phospholipids according to the present disclosure include, but are not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoy 1-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3- phospho-L-serine (sodium salt) (DPPS), 1,2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), 1-palmitoyl-2-oleoyl-sn-glycero-3-phosphoethanolamine (POPE), 1,2-distearoyl-sn-glycero-3-phosphoethanolamine (DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE).

Examples of phospholipids include, but are not limited to, dimyristoyl phosphatidylcholine (DMPC), 1,2-dilauroyl-sn-glycero-3-phosphocholine (DLPC), dipalmitoylphosphatidylcholine (DPPC), diolelphosphatidylglycerol (DOPG), 1,2-dioleoyl-sn-glycero-3-phosphatidylcholine (DOPC), 1,2-dioleoyl-sn-glycero-3-phosphatidylserine (DOPS), diolelphosphatidic acid (DOPA), egg phosphatidylcholine (egg PC), phosphatidylethanolamine (egg PE), 1-palmitoyl-2-oleoyl-sn-glycero-3-phosphatidylethanolamine (POPE), cardiolipin, and 1,2-dimyristoyl-sn-glycero-3-phosphate (sodium salt) (DMPA).

Suitable phospholipids according to the present disclosure are saturated phospholipids derived from two saturated long carbon chain fatty acids, wherein each fatty acid has a long carbon chain of at least 12 and no more than 20 carbons. In some embodiments, the suitable saturated phospholipids according to the present disclosure are selected from the group consisting of DLPC, DMPC, DPPC, and combinations thereof.

In some embodiments, the lipid mixture comprises suitable phospholipids according to the present disclosure, such as a positively or negatively charged phospholipid, and a determined amount of unsaturated phospholipid, wherein the determined amount is less than 10% molar percentage based on the total amount of phospholipids, for example, 9%, 8%, 7%, 6%, 5%, 4%, 3%, 2%, or 1%.

Local Anesthesia and Prophylactic Treatment of Pain

The anesthetic composition according to the present disclosure is for use in local anesthesia and can be administered perineurally or to a surgical wound to treat a pain. In some embodiments, the pain is postsurgical pain or labor pain. In some embodiments, the anesthetic composition is subcutaneously, intracutaneously, or intramuscularly administered to treat a painful condition in a subject in need thereof.

In some embodiments, the local anesthesia includes field block and infiltration anesthesia. The field block is directed to injecting a local anesthetic agent around the boundaries of the area to be anesthetized, with no attempt to locate specific nerves. The infiltration anesthesia is directed to injecting a local anesthetic agent directly into the area of terminal nerve endings.

In some embodiments, the composition according to the present disclosure is administered as a nerve block as prophylactic treatment of a painful condition, such as administration prior to surgery for the treatment of postsurgical pain, in a subject in need thereof.

A nerve block involves the introduction of an agent near or in a peripheral nerve for the reduction of pain or to provide numbness.

Types of nerve blocks include but are not limited to motor, sensory, differential, and autonomic blocks, and additionally, include but are not limited to brachial plexus (axillary, interscalene, supraclavicular, infraclavicular), individual upper extremity nerve blocks (median, radial, ulnar, musculocutaneous, axillary), sciatic, ankle, metatarsal, oral, femoral, popliteal fossa, saphenous, distal, digital, deep peroneal, superficial peroneal, tibial, sural, and saphenous blocks.

The disclosure will be further described with reference to the following specific, non-limiting examples.

EXAMPLES

The following examples illustrate the preparation and properties of certain embodiments of the present disclosure.

Example 1

Preparation of Ropivacaine Compositions with Various Phospholipids

Phospholipids, including DLPC, DMPC, DPPC, DOPG, DOPC, DOPS, DOPA, Egg PC, Egg PE, POPE, cardiolipin, and DMPA were purchased from NOF Corporation (Tokyo, Japan) or Lipoid GmbH (Ludwigshafen, Germany). Cholesterol was purchased from Sigma-Aldrich (Darmstadt, Germany) or Dishman Pharmaceuticals and Chemicals (Gujarat, India), and ropivacaine was purchased from Apollo Scientific (Cheshire, UK) or Dishman Pharmaceuticals and Chemicals. All other chemicals were purchased from Sigma-Aldrich.

To prepare lipid cakes, ropivacaine was combined with different lipid mixtures as indicated in Table 1 at a drug-to-phospholipid ratio (D:PL) of 1.458 µmol/µmol, i.e, phospholipid:cholesterol:ropivacaine=2:1:2.9. The lipids and ropivacaine were mixed and then dissolved in tert-butanol or a tert-butanol/water cosolvent system (1/1, vol/vol) to form the liquid structures. Each liquid structure sample was frozen for 30 to 60 minutes and then was lyophilized overnight to obtain a lipid cake.

To prepare the lipid structures for the vehicle control, a lipid mixture with a molar ratio of DMPC:cholesterol=2:1 was weighed and then dissolved in tert-butanol. The resulting sample was frozen for 60 minutes and then was lyophilized overnight to obtain a lipid cake of vehicle.

The lipid cakes were hydrated with 50 mM histidine buffers at pH 6.5 at a temperature no lower than 25° C./ambient temperature (AT) for 2 to 10 minutes to form vehicle and ropivacaine compositions respectively, followed by characterization of association efficiency and particle size distribution.

Example 2

Characterization of Ropivacaine Compositions

The association efficiency (AE) of each of the preparations described in Example 1 was determined as follows. Two hundred microliters of each ropivacaine composition were transferred to a centrifuge and spun for 5 min at 3000×g at 4° C. After decanting the supernatant, the separated lipid based complex was obtained and re-suspended to a final volume of 200 µL. A reference absorbance standard was established for each drug substance (e.g., ropivacaine) based on solutions of the test drug substance of known concentration. The amounts of drug substance of both the original ropivacaine composition and the separated lipid based complex were measured using an ultraviolet/visible (UV/Vis) spectrophotometer. The AE represents the ratio of the amount of drug substance in the separated lipid based complex to the amount of drug substance in the original ropivacaine composition. The D:PL of the separated lipid based complex was calculated by multiplying the D:PL of the lipid cake by AE and denoted as "resultant D:PL."

The particle size of each ropivacaine composition was measured using a laser diffraction particle size analyzer (LA-950V2, Horiba or Mastersizer 3000, Malvern). The volume median diameter (D50) of the lipid based complex containing ropivacaine formed by hydrating the lipid cake with 50 mM histidine buffer (pH 6.5) or phosphate buffer (pH 7.0) was examined and compared in Table 1.

The lipid cakes comprising DMPC, DLPC, or DPPC demonstrated very similar AE (90%, 90%, and 92%, respectively). However, the median diameter (D50) of the lipid based complex containing ropivacaine differed. The D50 of the resultant lipid based complex containing ropivacaine in the ropivacaine compositions from hydration of the lipid cakes with DMPC, DLPC, and DPPC was 6.6±0 to 12.7±0.4, 7.8±0.1, and 14.9±0.1 μm, respectively. A summary of the results is shown in Table 1.

TABLE 1

The AE and median diameter (D50) of selected ropivacaine compositions with various phospholipids.

| Lipid composition | Chain length/degree of unsaturation | D50 (μm) | AE (%) | Resultant D:PL |
|---|---|---|---|---|
| DMPC:cholesterol = 2:1[a] | 14:0/14:0 | 6.6 ± 0.0 | 96.1 | 1.40 |
| DMPC:cholesterol = 2:1[b] | 14:0/14:0 | 12.7 ± 0.4 | 90 | 1.32 |
| DLPC:cholesterol = 2:1[b] | 12:0/12:0 | 7.8 ± 0.1 | 90 | 1.32 |
| DPPC:cholesterol = 2:1[b] | 16:0/16:0 | 14.9 ± 0.1 | 92 | 1.34 |
| Egg PC:cholesterol = 2:1[b] | 16:0/18:1 | 5.7 ± 0.0 | N.A.* | N.A. |
| DOPG:cholesterol = 2:1[b] | 18:1/18:1 | 5.5 ± 0.4 | N.A. | N.A. |
| DOPC:cholesterol = 2:1[b] | 18:1/18:1 | 3.7 ± 0.0 | N.A. | N.A. |
| DOPS:cholesterol = 2:1[b] | 18:1/18:1 | 5.8 ± 0.1 | N.A. | N.A. |
| Cardiolipin:cholesterol = 2:1[b] | 18:1/18:1/18:1/18:1 | 15.3 ± 0.5 | N.A. | N.A. |

*N.A. (not applicable): The compositions could not be analyzed due to unacceptable viscosity, resulting in failure in the centrifugation step of the characterization protocol, even after extra centrifugation time had been applied.
[a]hydrated by phosphate buffer
[b]hydrated by histidine buffer Example 3

Preparation of Ropivacaine Compositions with Various Phospholipid Combinations

Sources of phospholipids, cholesterol, ropivacaine, and all other chemicals were described in Example 1.

To prepare lipid cakes, ropivacaine was combined with different lipid mixtures at the molar ratio of phospholipids: cholesterol:ropivacaine=2:1:2.9, where the phospholipids were a combination of DMPC and one of the other phospholipids described in Table 2 with molar ratio of DMPC:the other phospholipid=1.8:0.2. The lipids and ropivacaine were mixed and then dissolved in tert-butanol to form the liquid structures. Each liquid structure sample was frozen for 30 to 60 minutes and then was lyophilized overnight to obtain a lipid cake.

The lipid cakes were hydrated with 50 mM histidine buffers at pH 6.5 at ambient temperature to form ropivacaine compositions, followed by characterization of association efficiency and particle size distribution.

The resultant lipid based complex containing ropivacaine in the ropivacaine compositions from hydration of lipid cakes, which consists of a combination of DMPC/DLPC, DMPC/DPPC, DMPC/Egg PC, DMPC/Egg PE, or DMPC/POPE, demonstrated very similar AE (90%, 91%, 91%, 91%, and 91%, respectively). The median diameter (D50) of the lipid based complex containing ropivacaine in the ropivacaine compositions demonstrated similar results too. The D50 of the resultant lipid based complex in the ropivacaine compositions of the lipid cakes with a combination of DMPC/DLPC, DMPC/DPPC, DMPC/Egg PC, DMPC/Egg PE, or DMPC/POPE was 11.4±0.3, 14.3±0.1, 11.6±0.0, 11.5±0.0, and 11.0±0.3 μm, respectively. A summary of the results is shown in Table 2.

TABLE 2

The AE and median diameter (D50) of selected ropivacaine compositions with various phospholipid combinations.

| Lipid composition | D50 (μm) | AE (%) | Resultant D:PL |
|---|---|---|---|
| DMPC:DLPC:cholesterol = 1.8:0.2:1 | 11.4 ± 0.3 | 90 | 1.32 |
| DMPC:DPPC:cholesterol = 1.8:0.2:1 | 14.3 ± 0.1 | 91 | 1.32 |
| DMPC:Egg PC:cholesterol = 1.8:0.2:1 | 11.6 ± 0.0 | 91 | 1.32 |
| DMPC:Egg PE:cholesterol = 1.8:0.2:1 | 11.5 ± 0.0 | 91 | 1.33 |
| DMPC:POPE:cholesterol = 1.8:0.2:1 | 11.0 ± 0.3 | 91 | 1.32 |
| DMPC:DOPG:cholesterol = 1.8:0.2:1 | 9.5 ± 0.0 | N.A.* | N.A. |
| DMPC:DOPC:cholesterol = 1.8:0.2:1 | 8.2 ± 0.0 | N.A. | N.A. |
| DMPC:DOPS:cholesterol = 1.8:0.2:1 | 7.8 ± 0.0 | N.A. | N.A. |
| DMPC:DOPA:cholesterol = 1.8:0.2:1 | 8.1 ± 0.0 | N.A. | N.A. |
| DMPC:Cardiolipin:cholesterol = 1.8:0.2:1 | 6.6 ± 0.0 | N.A. | N.A. |
| DMPC:DMPA:cholesterol = 1.8:0.2:1 | 6.6 ± 0.0 | N.A. | N.A. |

*N.A. (not applicable): The compositions could not be analyzed due to unacceptable viscosity, resulting in failure in the centrifugation step of the characterization protocol, even after extra centrifugation time had been applied.

Example 4

Anesthetic Effect in a Paw Incision Rat Model

Sprague-Dawley rats were used for evaluating the anesthetic efficacy after paw incision as described in *Pain.* 1996

March; 64(3):493-501. The rat housing facility was operated on a 12-hour light/12-hour dark circadian cycle and experiments were performed during the day portion of the circadian cycle only. A ropivacaine composition as one embodiment of the anesthetic composition in accordance with the present disclosure (Ropivacaine composition) was prepared according to Example 1, wherein a lipid cake of DMPC:cholesterol:ropivacaine=2:1:2.9 was hydrated with 50 mM histidine buffer at pH 6.8. Unformulated ropivacaine was prepared by dissolving ropivacaine in water-for-injection at 19.0 mg/mL. A commercial FDA-approved extended release liposomal bupivacaine formulation (ER Bupivacaine) was purchased from Pacira Pharmaceuticals, Inc. The in vivo efficacy of Ropivacaine composition, unformulated ropivacaine, saline, and ER Bupivacaine was compared following intraplantar injection after paw incision at a dosage of 1.9 mg for unformulated ropivacaine and Ropivacaine composition and 1.33 mg for ER Bupivacaine (equipotent dosage) per incision.

Before surgery baselines (BBL) of 27 rats were measured −1 to −3 days prior to surgery; after surgery baselines (ABL) of 27 rats were measured 30 minutes after surgery. Rats displaying over 9 g baseline threshold value of BBL and less than 4 g baseline threshold value of ABL were used for formal studies. The final total of 20 rats were randomized into 4 groups (5 rats per group). While anesthetized with 2 to 3.5% isoflurane in 100% oxygen, each rat received a 1 cm longitudinal plantar incision on the left hind paw with another three incisions made on the fascia. Each rat received a single intra-plantar injection of saline (100 μl), Ropivacaine composition (100 μl of 19.0 mg/mL), ER Bupivacaine (100 μl of 13.3 mg/mL), or unformulated ropivacine (100 μl of 19.0 mg/mL). The 50% paw withdrawal threshold of each rat was obtained using the Dixon up-down method at BBL time point (−1 to −3 days), ABL time point, and the designated time points (0.5, 1, 2, 3, 4, 5, 6, 7 and 24 hours) after intra-plantar injection.

Figure 1B:
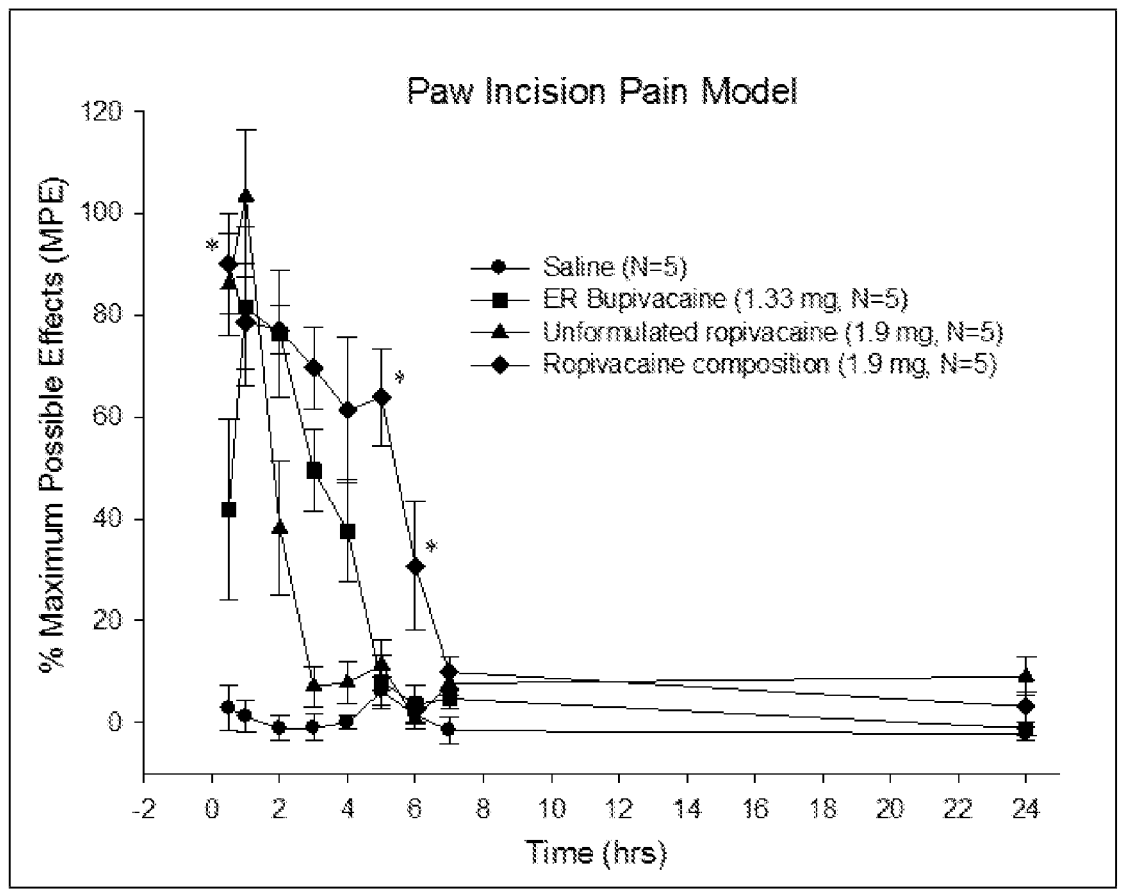
FIG. 1B is a graph depicting the percentage of maximum possible effects (% MPE), calculated from the 50% paw withdrawal threshold using the formula % MPE=(Threshold$_{aftertreatment}$−ABL)/(BBL−ABL)×100%; wherein the error bars represent the standard error of mean (SEM); *:P<0.05 when compared to ER Bupivacaine group. MPE over 30% is considered effective.

The anesthetic efficacy of Ropivacaine composition (diamond), unformulated ropivacaine (triangle), ER Bupivacaine (square), and Saline (circle) after paw incision is shown in FIG. 1A and FIG. 1B. The average 50% paw withdrawal threshold for each treatment group was graphed; data presented as 50% paw withdrawal threshold (g) were plotted against time (FIG. 1A). The percentage of maximum possible effect (% MPE) of each treatment was calculated from 50% paw withdrawal threshold using the formula % MPE=(Threshold$_{after\ treatment}$−ABL)/(BBL−ABL)×100%. The % MPE for each treatment was graphed; data presented as a MPE were plotted against time (FIG. 1B). The onset time of Ropivacaine composition and unformulated ropivacaine was similar, with the withdrawal threshold increased from 1.83 g to 13.00 g and 1.74 g to 11.47 g, respectively, at the T=0.5 hour time point. The onset time of Ropivacaine composition was earlier than ER Bupivacaine, which displayed an increased withdrawal threshold from 1.80 g to 6.51 g at the T=0.5 hour time point. Ropivacaine composition produced the longest analgesic action (lasting for at least 6 hours) compared to ER Bupivacaine (less than 5 hours).

Example 5

Anesthetic Effect in a Cuff-Implanted Sciatic Nerve Pain Rat Model

Sprague-Dawley rats were used for evaluating the anesthetic efficacy after cuff-implanted on sciatic nerve as described in Pain. 1999 October; 83(1):37-46. The rat housing facility was operated on a 12-hour light/12-hour dark circadian cycle and experiments were performed during the day portion of the circadian cycle only. A ropivacaine composition as one embodiment of the anesthetic composition in accordance with the present disclosure (Ropivacaine composition) was prepared according to Example 1, wherein a lipid cake of DMPC:cholesterol:ropivacaine=2:1:2.9 were hydrated with 50 mM histidine buffer at pH 6.8. A commercial FDA-approved extended release liposomal bupivacaine formulation (ER Bupivacaine) was purchased from Pacira Pharmaceuticals, Inc. The in vivo efficacy of Ropivacaine composition, ER Bupivacaine, and saline was compared following sciatic nerve injection technique after cuff-implanted on the sciatic nerve of rats at the dosage of 25 mg/kg for Ropivacaine composition and 25 mg/kg and 35 mg/kg for ER Bupivacaine.

While anesthetized, a 3 mm to 4 mm PE 60 or PE 90 tube was placed onto the sciatic nerve of the left leg. The muscle and skin were apposed with 2 to 3 sutures after cuffing. After cuff-implanted baseline (2 to 3 weeks after cuff-implantation) was collected to confirm pain induction. Rats displaying less than a 4 g baseline threshold value were used for formal studies. A total of 21 rats were randomly divided into 3 groups (of 7 rats each), and received Ropivacaine composition (25 mg/kg), ER Bupivacaine (25 mg/kg), or ER Bupivacaine (35 mg/kg) via sciatic nerve dosing blockage technique. Four rats received saline treatments as control. The 50% paw withdrawal threshold of each rat was obtained using the Dixon up-down method at pre-dosing and the designated time points (1, 3, 4, 5, 6, 7, 8, and 9 hrs) after dosing.

Figure 2A:
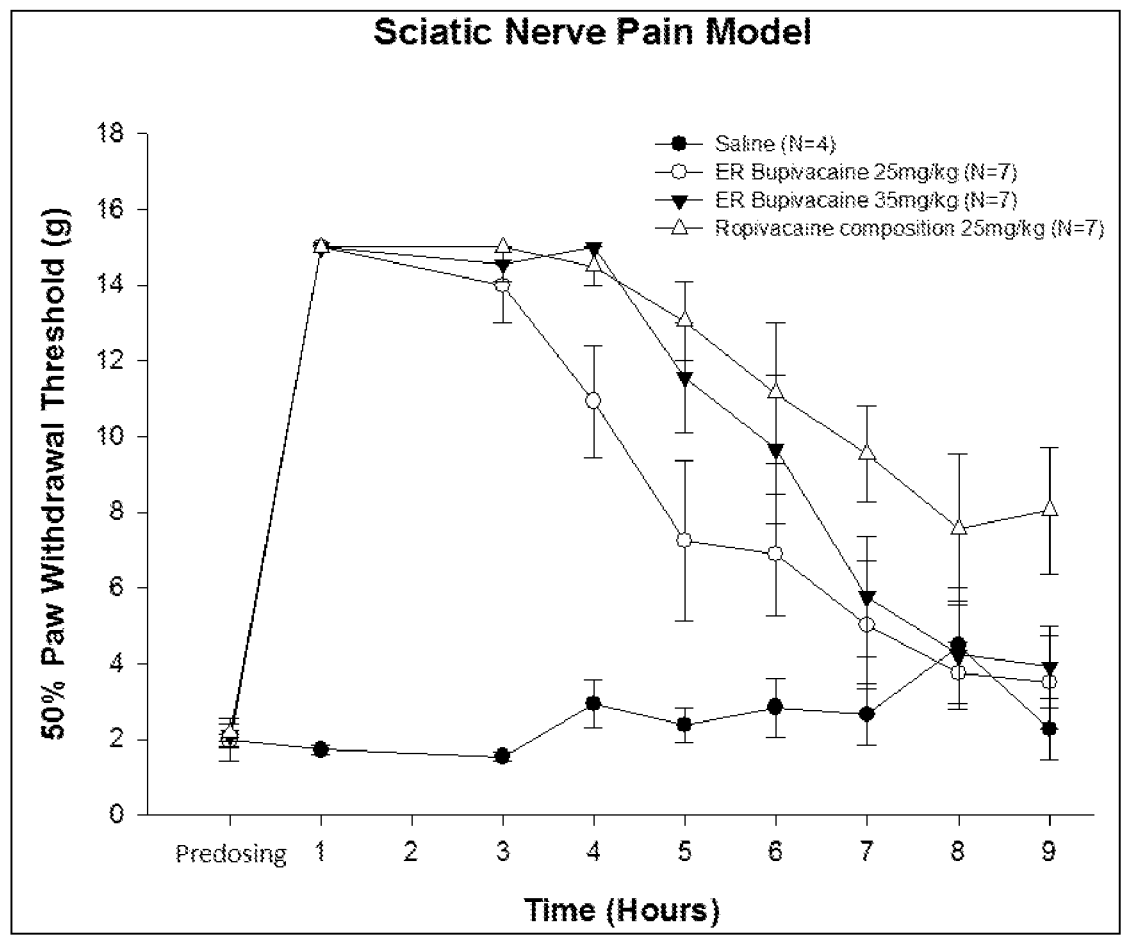
FIG. 2A is a graph depicting the 50% paw withdrawal threshold by a Von Frey test, wherein an anesthetic composition in accordance with the present disclosure (Ropivacaine composition) is our test article and ER Bupivacaine are used as reference articles. Saline, Ropivacaine composition, and ER Bupivacaine were administered via sciatic nerve blockage technique. Error bars represent the standard error of mean (SEM)
Figure 2B:
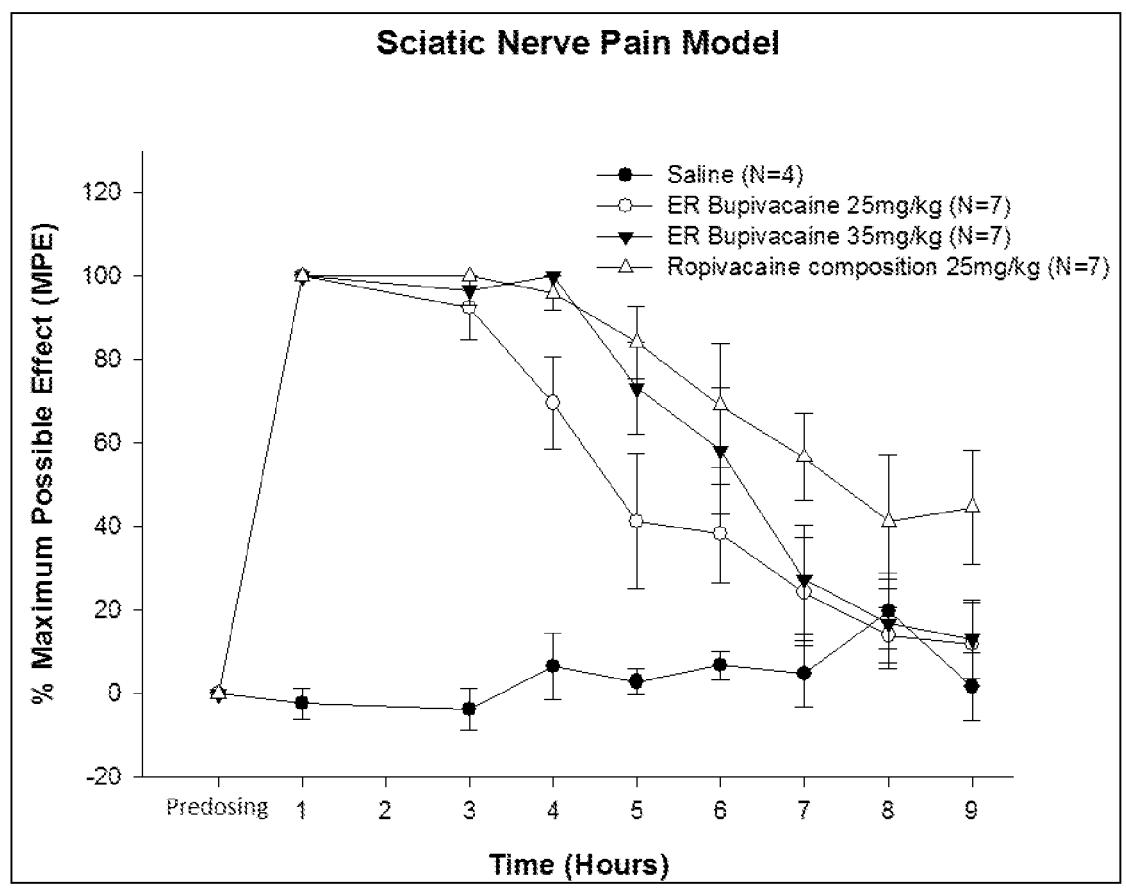
FIG. 2B is a graph depicting the percentage of maximum possible effects (% MPE), which were calculated from the 50% paw withdrawal threshold by the formula % MPE=(Threshold$_{after\ treatment}$−Predosing Baseline)/(Threshold$_{Cut-off}$−Predosing Baseline)×100%, cut-off threshold was 15 g. Error bars represent the standard error of mean (SEM). MPE over 30% is considered effective.

The anesthetic efficacy of Ropivacaine composition (25 mg/kg, open triangle), ER Bupivacaine (25 mg/kg, open circle; 35 mg/kg, closed inverted triangle), and saline (closed circle) after dosing is shown in FIG. 2A and FIG. 2B. The average 50% paw withdrawal threshold for each treatment group was graphed; data presented as 50% paw withdrawal threshold (g) were plotted against time (FIG. 2A). The percentage of maximum possible effect (% MPE) of each treatment was calculated from 50% paw withdrawal threshold using the formula % MPE= (Threshold$_{after\ treatment}$−Predosing Baseline)/(Threshold$_{Cut-off}$−Predosing Baseline)×100%. The cut-off threshold was 15 g in this study. The % MPE for each treatment was graphed; data presented as a % MPE were plotted against time (FIG. 2B). Ropivacaine composition produced the longest (>9 hours) analgesic action compared to ER Bupivacaine (less than 8 hours) for both the 25 mg/kg and 35 mg/kg groups. A percentage of MPE of over 30% was considered effective.

What is claimed is:

1. An anesthetic composition, comprising:
  a lipid based complex comprising ropivacaine base and a lipid mixture including at least one phospholipid in the presence of an aqueous buffer at a pH of 5.5 to 8.0, wherein the at least one phospholipid is derived from saturated fatty acids, each fatty acid independently comprising a carbon chain of carbon number no greater than 18;
  wherein the lipid based complex has a median diameter of no less than 1 μm, and the molar ratio of ropivacaine base to phospholipid is at least 0.5:1.

2. The anesthetic composition of claim 1, wherein the phospholipid is selected from the group consisting of dimyristoyl phosphatidylcholine (DMPC), 1,2-dilauroyl-sn-glycero-3-phosphocholine (DLPC), and dipalmitoylphosphatidylcholine (DPPC).

3. The anesthetic composition of claim 1, wherein the lipid mixture further comprises an unsaturated phospholipid present in an amount less than 10% molar percentage based on the amount of the total phospholipids.

4. The anesthetic composition of claim 1, wherein the lipid mixture consists essentially of neutral saturated phospholipids and sterol.

5. The anesthetic composition of claim 1, wherein the lipid mixture comprises sterol.

6. The anesthetic composition of claim 5, wherein the mole percentage of sterol in the lipid mixture is not more than 50%.

7. The anesthetic composition of claim 5, wherein the at least one phospholipid and sterol are at a molar ratio of from 1:0.01 to 1:1.

8. The anesthetic composition of any one of claims 5 to 7, wherein the sterol is cholesterol.

9. The anesthetic composition of any one of claims 1, 2, 3, 4, and 5 to 7, wherein the median diameter of the lipid based complex is at a range selected from the group consisting of from 5 μm to 50 μm, 5 μm to 40 μm, 5 μm to 30 μm, 5 μm to 20 μm, and 5 μm to 15 μm.

10. A method for treating pain in a subject in need of anesthetization via a nerve block, via an infiltration anesthesia, or via a field block, comprising administering to the subject an effective amount of the anesthetic composition of any one of claims 1, 2, 3, 4, and 5-8.

11. The anesthetic composition for use of claim 10, wherein the lipid mixture consists essentially of one or more neutral saturated phospholipids.

12. The anesthetic composition of claim 10, wherein the saturated phospholipid is selected from the group consisting of dimyristoyl phosphatidylcholine (DM PC), 1,2-dilauroyl-sn-glycero-3-phosphocholine (DLPC), and dipalmitoylphosphatidylcholine (DPPC).

13. A method for producing analgesia or pain relief in a subject in need thereof, comprising administering to the subject the anesthetic composition of any one of claims 1, 2, 3, 4, 5 to 8, 9, and 10 to 12.

14. A method for managing pain or for prophylactic treatment of pain in a subject, comprising administering to the subject the anesthetic composition of any one of claims 1, 2, 3, 4, 5 to 8, 9, and 10 to 12.

15. The anesthetic composition of claim 1, wherein the molar ratio of ropivacaine base to phospholipid in the lipid based complex is at least 0.9:1.

16. The anesthetic composition of claim 1, wherein the molar ratio of ropivacaine base to phospholipid in the lipid based complex is at least 1.1:1.

17. The anesthetic composition of claim 1, wherein the molar ratio of ropivacaine base to phospholipid in the lipid based complex is at least 1.3:1.

* * * * *

UNITED STATES PATENT AND TRADEMARK OFFICE
CERTIFICATE OF CORRECTION

PATENT NO. : 11,938,220 B2
APPLICATION NO. : 17/043920
DATED : March 26, 2024
INVENTOR(S) : Keelung Hong et al.

It is certified that error appears in the above-identified patent and that said Letters Patent is hereby corrected as shown below:

In the Claims

Claim 12, Column 14, Line 6, "(DM PC)" should read --(DMPC)--.

Signed and Sealed this
Twenty-eighth Day of May, 2024

Katherine Kelly Vidal
*Director of the United States Patent and Trademark Office*